(12) United States Patent
Jung et al.

(10) Patent No.: US 10,559,838 B2
(45) Date of Patent: Feb. 11, 2020

(54) OXYGEN SENSING DEVICE WITH CAPABILITY OF STORING ENERGY, RELEASING ENERGY, GENERATING SPECIFIC GAS AND REMOVING HARMFUL GAS

(71) Applicant: YUAN ZE UNIVERSITY, Taoyuan County (TW)

(72) Inventors: Guo-Bin Jung, Taoyuan County (TW); Cheng-You Lin, Taichung (TW); Bo-Wei Huang, Taichung (TW); Shih-Yua Sun, Hsinchu (TW); Shih Hung Chan, Taoyuan County (TW)

(73) Assignee: YUAN ZE UNIVERSITY, Taoyuan County (TW)

( * ) Notice: Subject to any disclaimer, the term of this patent is extended or adjusted under 35 U.S.C. 154(b) by 373 days.

(21) Appl. No.: 15/411,770

(22) Filed: Jan. 20, 2017

(65) Prior Publication Data

US 2017/0133695 A1    May 11, 2017

Related U.S. Application Data

(63) Continuation-in-part of application No. 13/572,147, filed on Aug. 10, 2012, now abandoned.

(30) Foreign Application Priority Data

Feb. 17, 2012   (TW) .............................. 101105241 A

(51) Int. Cl.
*H01M 8/04302* (2016.01)
*G01N 27/409* (2006.01)
(Continued)

(52) U.S. Cl.
CPC ......... *H01M 8/04302* (2016.02); *B60L 50/72* (2019.02); *B60L 53/24* (2019.02);
(Continued)

(58) Field of Classification Search
CPC ......... H01M 8/04304; H01M 8/04552; H01M 8/0612; H01M 16/006; H01M 2008/1293;
(Continued)

(56) References Cited

U.S. PATENT DOCUMENTS

| | | | |
|---|---|---|---|
| 2007/0034426 A1* | 2/2007 | Akamatsu | B82Y 10/00 123/3 |
| 2010/0033140 A1* | 2/2010 | Otake | B60L 3/04 320/165 |
| 2013/0213806 A1* | 8/2013 | Jung | G01N 27/409 204/406 |

* cited by examiner

*Primary Examiner* — Maris R Kessel
(74) *Attorney, Agent, or Firm* — Li & Cai Intellectual Property (USA) Office

(57) ABSTRACT

An oxygen sensing device with capability of storing energy and releasing energy including an oxygen sensing unit, a gas storing unit, and a control unit. The oxygen sensing unit includes a solid oxide electrolyte disposed between two conductive catalyst layers. The control unit includes a power source, a voltmeter, and a power output circuit. The power source provides electrical power to these conductive catalyst layers of the oxygen sensing unit to process a catalytic reaction and generate hydrocarbons for being stored in the gas storing unit. The voltmeter senses a voltage generated by the oxygen sensing unit when the oxygen sensing unit senses oxygen. The oxygen sensing unit makes the hydrocarbons stored in the gas storing unit and oxygen process a chemical reaction for generating electrical power to the power output circuit. The oxygen sensing unit uses the power source to generate hydrogen or syngas.

7 Claims, 12 Drawing Sheets

(51) Int. Cl.
    *G01N 27/407*     (2006.01)
    *H01M 8/04537*     (2016.01)
    *H01M 16/00*     (2006.01)
    *H01M 8/0612*     (2016.01)
    *F01N 3/10*     (2006.01)
    *F01N 5/02*     (2006.01)
    *B60L 50/72*     (2019.01)
    *B60L 53/24*     (2019.01)
    *H01M 8/124*     (2016.01)

(52) U.S. Cl.
    CPC ............... *F01N 3/10* (2013.01); *F01N 5/025* (2013.01); *G01N 27/409* (2013.01); *G01N 27/4073* (2013.01); *H01M 8/04552* (2013.01); *H01M 8/0612* (2013.01); *H01M 16/006* (2013.01); *H01M 2008/1293* (2013.01)

(58) Field of Classification Search
    CPC . B60L 50/72; B60L 53/24; F01N 3/10; F01N 5/025; G01N 27/4073; G01N 27/409
    See application file for complete search history.

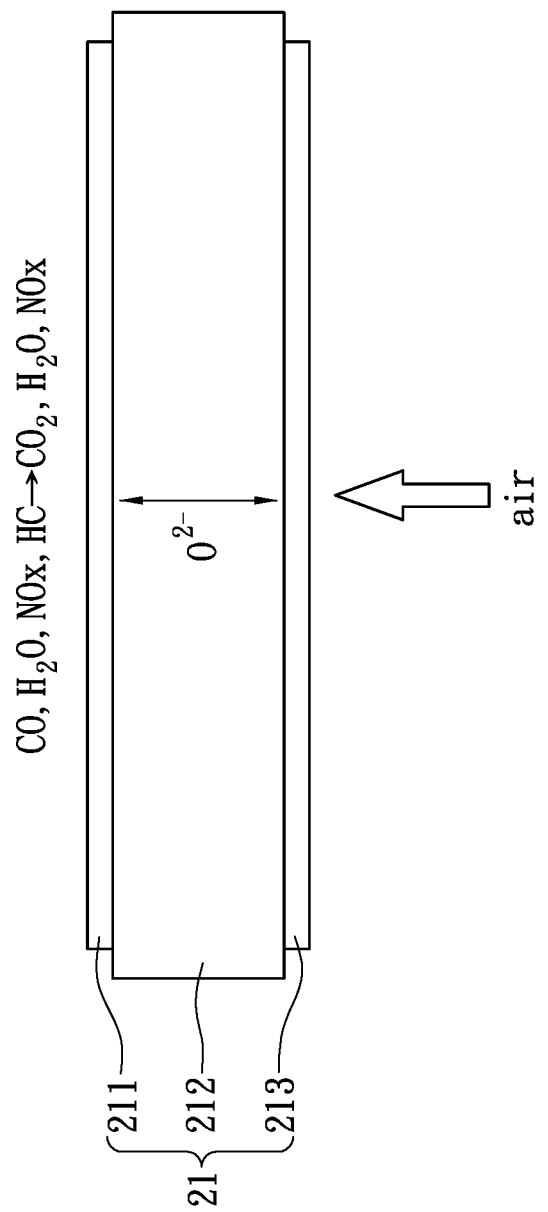

OXYGEN SENSING DEVICE WITH CAPABILITY OF STORING ENERGY, RELEASING ENERGY, GENERATING SPECIFIC GAS AND REMOVING HARMFUL GAS

BACKGROUND OF THE INVENTION

1. Field of the Invention

The instant disclosure relates to an oxygen sensing device; in particular, to an oxygen sensing device with capability of storing energy and releasing energy utilized for removing pollutants, output electricity, storing electrical energy, and making specific chemicals.

2. Description of Related Art

FIG. 1A shows a schematic diagram of a traditional fuel converting mechanism of a car. The traditional fuel converting mechanism in a car comprises an alternator 10, an internal combustion engine 11, a turbine 12, an oxygen sensing device 13 and a catalytic converter 14. The internal combustion engine 11 makes the combustion of air and fuel (e.g. hydrocarbons) and generates gas such as carbon dioxide, carbon monoxide, water, and nitrogen monoxide . . . etc. Then, the internal combustion engine 11 outputs the mentioned gas ($CO_2$, CO, $H_2O$, and NO . . . etc.) to the turbine 12. The turbine 12 cooperates with the alternator 10 to generate electrical energy. The oxygen sensing device 13 senses the oxygen outputted from the turbine 12 and generates a control signal A/F for adjusting the ratio of the air and the fuel transmitted to the internal combustion engine 11. The catalytic converter 14 converts the carbon monoxide (CO), hydrogencarbons (HCs) and nitrogen monoxide (NO) outputted from the turbine 12 to carbon dioxide ($CO_2$) and nitrogen ($N_2$) for complying with environmental standards.

FIG. 1B shows a schematic diagram of a traditional oxygen sensing device. The traditional oxygen sensing device 13 comprises an oxygen sensing unit 130 and a voltmeter 131. The oxygen sensing unit 130 comprises a conductive catalyst layer 132, a solid oxide electrolyte 133 and a conductive catalyst layer 134. The solid oxide electrolyte 133 is disposed between the conductive catalyst layer 132 and the conductive catalyst layer 134. The conductive catalyst layer 132 receives the gas from the turbine 12. The oxygen concentration of the gas from the turbine 12 is unknown. The conductive catalyst layer 134 receives air from the atmosphere with oxygen concentration of 0.21 atm. A voltage difference would be occurred between the conductive catalyst layer 132 and the conductive catalyst layer 134, and the voltage difference could be measured by the voltmeter 131. When the oxygen concentration of the gas from the turbine 12 is less, the voltmeter 131 could sense a larger voltage difference. On the contrary, when the oxygen concentration of the gas from the turbine 12 is more, the voltmeter 131 could sense a smaller voltage difference. Accordingly, the oxygen sensing device 13 generates the control signal A/F to adjust the ratio (A/F) of the air and the fuel transmitted to the internal combustion engine 11. Therefore, the combustion process in the internal combustion engine 11 could be adjusted.

However, the traditional oxygen sensing device 13 has only the aforementioned single-function, thus applications of the oxygen sensing device 13 may be limited thereto.

SUMMARY OF THE INVENTION

The object of the instant disclosure is to offer an oxygen sensing device with capability of storing energy and releasing energy for processing chemical reactions, such as catalytic reaction, oxygen sensing, power generation, electrolysis for storing energy and electrolysis for making synthesis gas.

In order to achieve the aforementioned objects, according to an embodiment of the instant disclosure, an oxygen sensing device is offered. The oxygen sensing device comprises an oxygen sensing unit, a gas storing unit and a control unit. The oxygen sensing unit comprises a first conductive catalyst layer, a second conductive catalyst layer and a solid oxide electrolyte. The solid oxide electrolyte is disposed between the first conductive catalyst layer and the second conductive catalyst layer. The control unit comprises a voltmeter, a power output circuit, a power source and a judgment circuit. The voltmeter senses a voltage generated between the first conductive catalyst layer and the second conductive catalyst layer when the oxygen sensing unit senses the oxygen concentration difference. The power output circuit outputs an electric power, wherein the oxygen sensing unit causes a reaction of the hydrocarbons stored in the gas storing unit and the oxygen for generating the electric power to the power output circuit. The judgment circuit controls conducting status of a power source, the voltmeter, or the power output circuit through at least a switch. The judgment circuit controls the gas storing unit to store the gas generated by the oxygen sensing unit or provide the gas to the gas sensing unit, wherein the electric power is provided to the first conductive catalyst layer of the oxygen sensing unit for processing a catalytic reaction to generate hydrocarbons. The oxygen sensing unit utilizes the electric power of power source of the control unit to generate hydrogen or carbon monoxide.

In summary, the oxygen sensing device according to an embodiment of the instant disclosure could process catalytic reaction, oxygen sensing, electrical energy generating, electrolysis for storing energy and making synthesis gas (carbon monoxide and hydrogen). Therefore, pollution exhaust could be decreased, pollution exhaust could be used for power generation, the surplus electricity could be used, or the industrial synthesis gas (carbon monoxide and hydrogen) could be made too.

In order to further the understanding regarding the instant disclosure, the following embodiments are provided along with illustrations to facilitate the disclosure of the instant disclosure.

BRIEF DESCRIPTION OF THE DRAWINGS

FIG. 5A shows a schematic diagram of an oxygen sensing unit processing the reaction of hydrocarbons and oxygen according to an embodiment of the instant disclosure;

DETAILED DESCRIPTION OF THE PREFERRED EMBODIMENTS

The aforementioned illustrations and following detailed descriptions are exemplary for the purpose of further explaining the scope of the instant disclosure. Other objectives and advantages related to the instant disclosure will be illustrated in the subsequent descriptions and appended drawings.

This embodiment offers an oxygen sensing device could process chemical reactions, such as catalytic reaction, oxygen sensing, electrical power generation, electrolysis for storing energy and electrolysis for making synthesis gas. The oxygen sensing device could be installed in a car or a power plant, and the oxygen sensing device can process one of the aforementioned reactions according to usage requirements.

Figure 2:
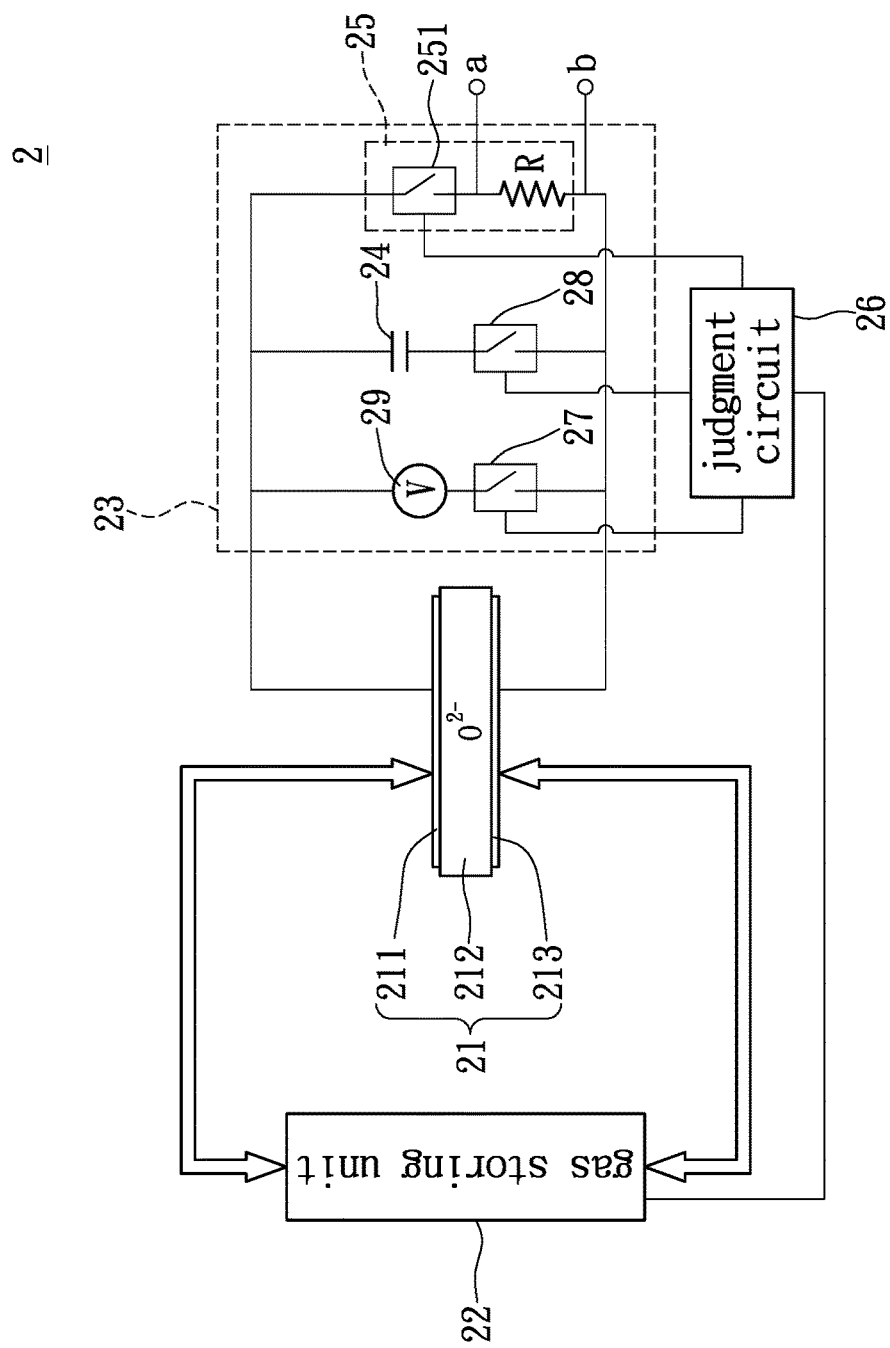
FIG. 2 shows a schematic diagram of an oxygen sensing device according to an embodiment of the instant disclosure.

FIG. 2 shows a schematic diagram of an oxygen sensing device according to an embodiment of the instant disclosure. The oxygen sensing device 2 comprises an oxygen sensing unit 21, a gas storing unit 22 and a control unit 23. The oxygen sensing unit 21 comprises a solid oxide electrolyte 212, a conductive catalyst layer 211 and a conductive catalyst layer 213. The control unit 23 comprises a power source 24, a voltmeter 29, a power output circuit 25, a judgment circuit 26 and switches 27, 28. The power output circuit 25 comprises a switch 251 and a resistor R.

The solid oxide electrolyte 212 is disposed between the conductive catalyst layer 211 and the conductive catalyst layer 213. The gas storing unit 22 is connected to the conductive catalyst layer 211 and the conductive catalyst layer 213 of the oxygen sensing unit 21. The oxygen sensing unit 21 is electrically coupled the control unit 23. The power source 24, the voltmeter 29 and the power output circuit 25 of the control unit 23 are connected in parallel and electrically coupled to the conductive catalyst layer 211 and the conductive catalyst layer 213. The switch 251 and the resistor R of the power output circuit 25 are connected serially. The switch 27 and the switch 28 are serially connected to the voltmeter 29 and the power source 24 respectively. The judgment circuit 26 is electrically coupled to the switches 251, 27, and 28 and the gas storing unit 22.

The solid oxide electrolyte 212 of the oxygen sensing unit 21 may be metal oxides, such as $ZrO_2$, $CeO_2$ . . . etc. The conductive catalyst layer 211, 213 may comprise metal catalyst, oxide catalyst or metal oxide catalyst. The metal catalyst may be Platinum (Pt), Rhodium (Rh), or Palladium (Pd). Platinum (Pt) and Rhodium (Rh) are catalyst for converting the oxides of nitrogen ($NO_x$) to nitrogen ($N_2$) and oxygen ($O_2$). Palladium (Pd) is catalyst for converting the carbon monoxide (CO) to carbon dioxide ($CO_2$). The oxide catalyst may be Lanthanum-Strontium-Cobalt pervoskite, for example, the Lanthanum-Strontium-Manganese oxide (LaSrMnO) may catalyze reaction of oxygen ion ($O^{2-}$) with oxides of nitrogen ($NO_x$), Methane ($CH_4$), or carbon monoxide (CO). The metal oxide catalyst may be Zirconia ($ZrO_2$) or Cerium oxide ($CeO_2$). The conductive catalyst layer 211, 213 may be conductors or carriers with large surface area (e.g. Alumina, Zeolite) coated with aforementioned metal catalyst, oxide catalyst or metal oxide catalyst.

The gas storing unit 22 receives the exhausted gas (generated by the internal combustion engine) transmitted from the turbine. The gas storing unit 22 is controlled by the judgment circuit 26 for transmitting the gas stored in the gas storing unit 22 to the oxygen sensing unit 21 or storing the gas generated by the oxygen sensing unit 21. The gas storing unit 22 may comprise at least a two-way valve (not shown in the figure) to make the gas flowing between the gas storing unit 22 and the oxygen sensing unit 21. Those skilled in the art will readily observe the valve of the gas storing unit 22, thus there is no need to go into details.

The power output circuit 25 comprises the switch 251 and the resistor R. The power output circuit 25 has output terminals a, b. Electrical equipment (not shown in the figure) could be connected to the output terminals a, b for obtaining electrical power. The switch 251 is controlled by the judgment circuit 26. When the switch 251 is conductive, the power output circuit 25 and the electrical equipment could perform a conducting loop. The resistor R of the power output circuit 25 is an output resistance for adjusting the output power.

The judgment circuit 26 is for controlling the oxygen sensing device 2 to perform functions, and the judgment circuit 26 may be connected to exterior interface (not shown in the figure). A user may manipulate the interface to make commands (or controlling signals) to the judgment circuit 26 of the oxygen sensing device 2, and the judgment circuit 26 could determine to execute corresponding functions according to the commands (or controlling signals). According to the executed function of the oxygen sensing device 2, the judgment circuit 26 controls the conducting state of the switches 251, 27, and 28. The judgment circuit 26 controls the power output circuit 25, the voltmeter 29, and the power source 24 through the switches 251, 27, and 28. The judgment circuit 26 may also controls the gas storing unit 22 to store the gas generated by the oxygen sensing unit 21, or makes the gas storing unit 22 provide gas to the oxygen sensing unit 21. In practical applications, the judgment circuit 26 may be accomplished by a micro controller unit (MCU), however the instant disclosure is not restricted thereto.

Figure 3A:
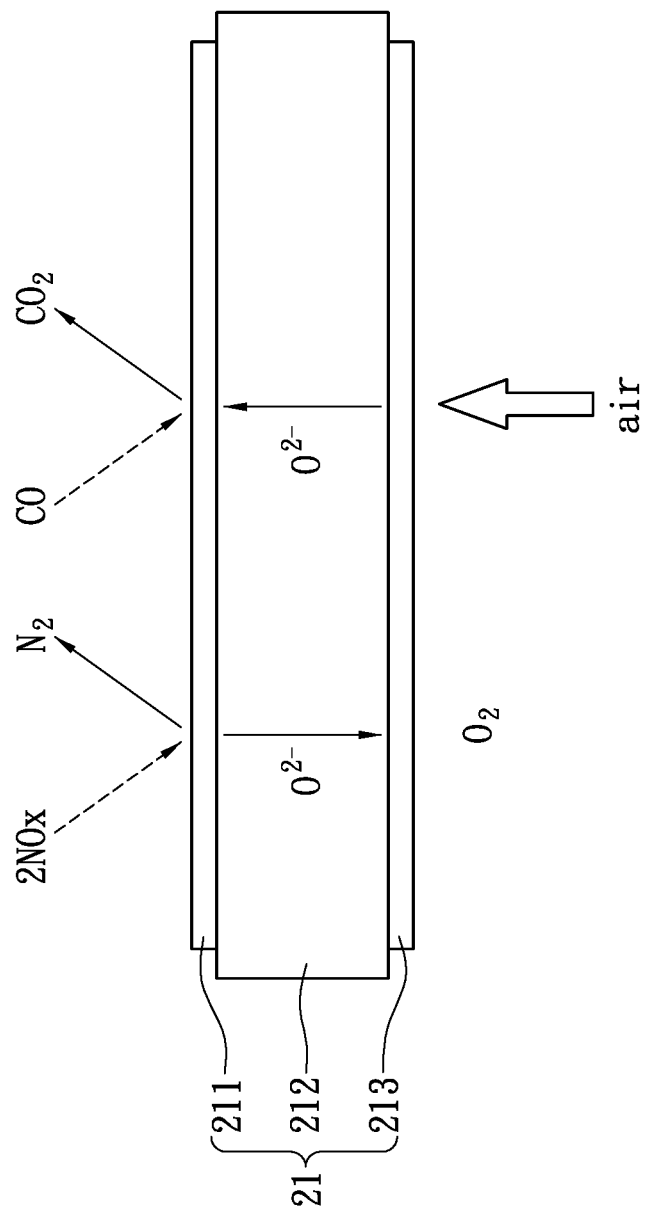
FIG. 3A shows a schematic diagram for an electrochemical catalytic reaction of an oxygen sensing unit according to an embodiment of the instant disclosure.
Figure 3B:
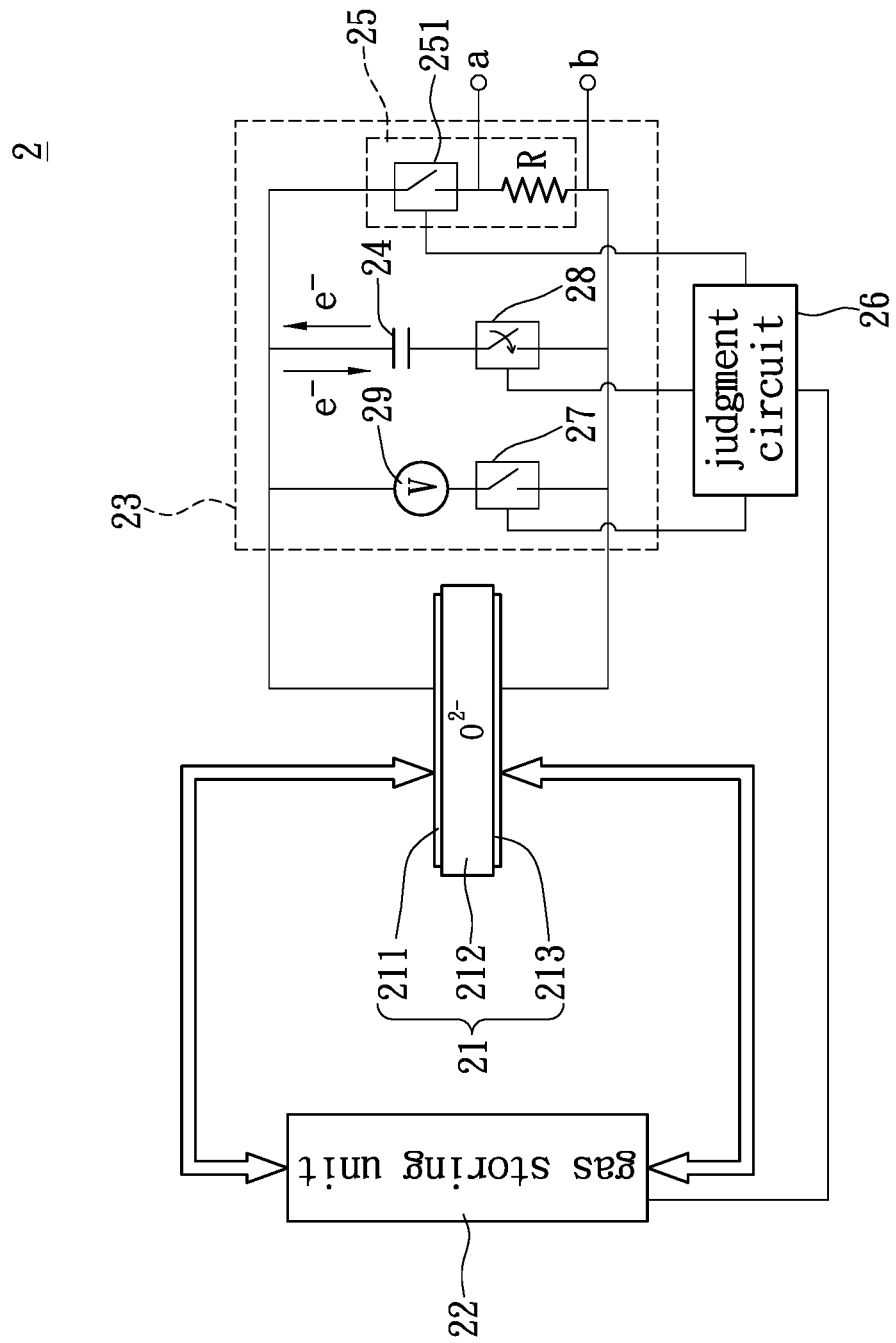
FIG. 3B shows a schematic diagram of the operation for an electrochemical catalytic reaction of an oxygen sensing device according to an embodiment of the instant disclosure.

Please refer to FIG. 3A and FIG. 3B, FIG. 3A shows a schematic diagram for an electrochemical catalytic reaction of an oxygen sensing unit according to an embodiment of the instant disclosure, FIG. 3B shows a schematic diagram of the operation for an electrochemical catalytic reaction of an oxygen sensing device according to an embodiment of the instant disclosure. When the oxygen sensing device 2 processes the electrochemical catalytic reaction, the conductive catalyst layer 211 of the oxygen sensing unit 21 may process catalytic reaction of oxides of nitrogen ($NO_x$) and carbon monoxide (CO) exhausted from the turbine (not shown in the figure) of the car. The gas exhausted from the turbine may be transmitted to the gas storing unit 22, then the judgment circuit 26 of the control unit 23 makes the exhausted gas stored in the gas storing unit 22 be transmitted to the conductive catalyst layer 211. For example, the judgment circuit 26 may open the valve between the conductive catalyst layer 211 and the gas storing unit 22 to make the exhausted gas be transmitted to the conductive catalyst layer 211. When judgment circuit 26 conducts the switch 28, the power source 24 could provide electrical power (electrons e−) to the conductive catalyst layer 211 of the oxygen sensing unit 21 for processing the catalytic reaction to generate hydrocarbons, and the hydrocarbons may be stored to the gas storing unit 22. For example, when the conductive catalyst layer 211 comprises Platinum (Pt), Rhodium (Rh) and Palladium (Pd), the oxides of nitrogen ($NO_x$) in the exhausted gas could make a reaction (1) through the catalyst of Platinum (Pt) and Rhodium (Rh), the reaction (1) is described in the following: $2NO_x+2e^-\rightarrow O^{2-}+N_2$.

In the reaction (1), the oxides of nitrogen ($NO_x$) is converted to nitrogen ($N_2$). Additionally, the oxygen ions ($O^{2-}$) can be transmitted to the conductive catalyst layer 213 through the solid oxide electrolyte 212. And, the conductive catalyst layer 213 converts the oxygen ions ($O^{2-}$) into oxygen ($O_2$) and transmits the excess electrons e− to the power source 24. On the other hand, the catalyst of Palladium (Pd) makes a reaction (2) of carbon monoxide (CO) of the exhausted gas, the reaction (2) is described in the following: $CO+O^{2-}\rightarrow CO_2+2e^-$.

The solid oxide electrolyte 212 conducts oxygen ions ($O^{2-}$) needed in the reaction (2), and the electrons (e−) generated in the reaction (2) may be transmitted to the power source 24 through the conductive catalyst layer 211. It is worth mentioning that when the switch 28 is conductive, the switch 27 and the switch 251 are non-conductive.

Figure 4:
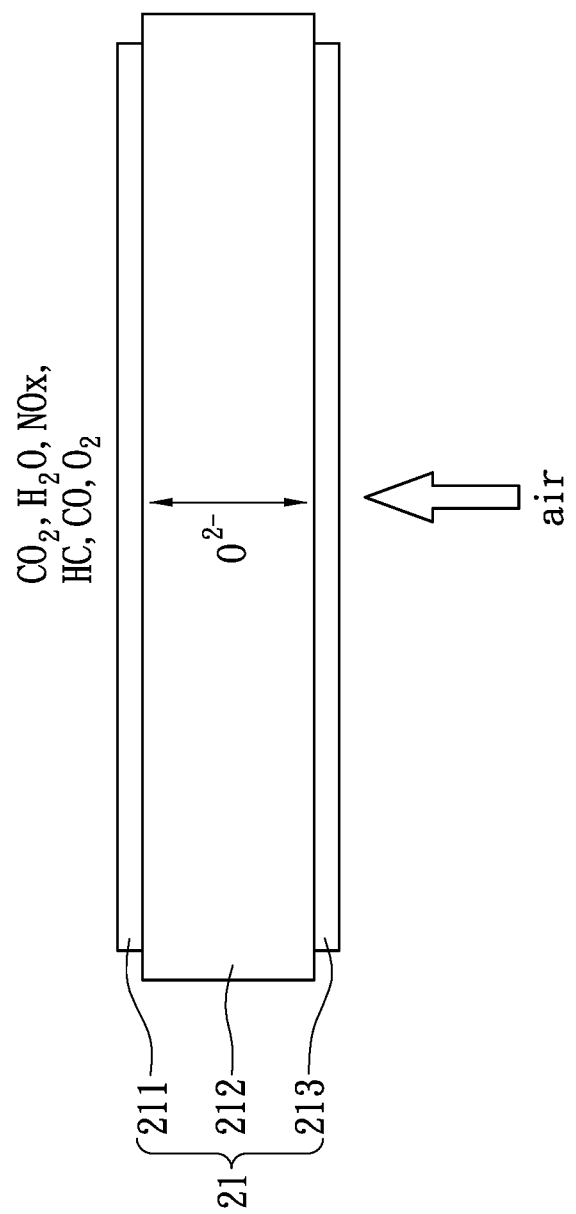
FIG. 4 shows a schematic diagram of an oxygen sensing unit processing the oxygen sensing according to an embodiment of the instant disclosure.

Please refer to FIG. 2 and FIG. 4, FIG. 4 shows a schematic diagram of an oxygen sensing unit processing the oxygen sensing according to an embodiment of the instant disclosure. The judgment circuit 26 of the control unit 23 conducts the switch 27 to make the voltmeter 29 for sensing the voltage difference between the conductive catalyst layer 211 and the conductive catalyst layer 213. Meanwhile, the switch 28 and the switch 251 are non-conductive.

Figure 1A:
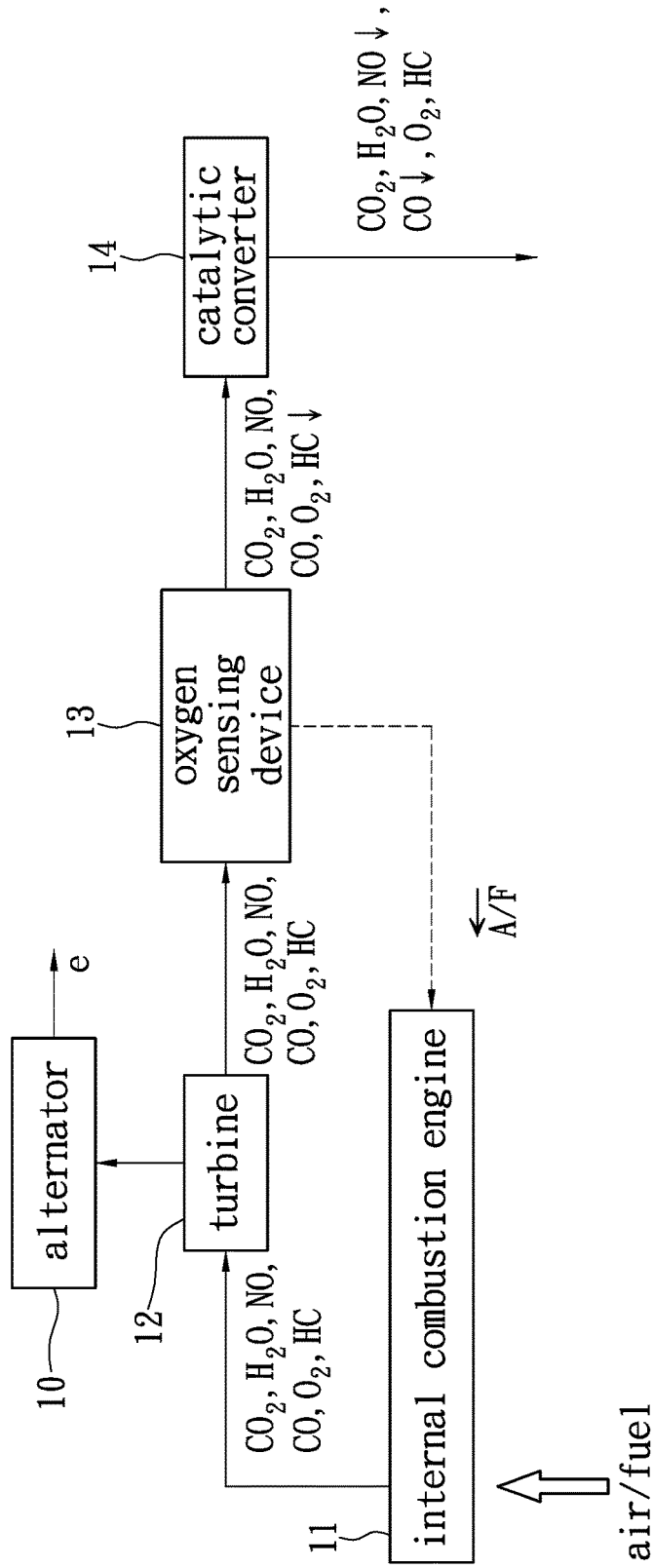
FIG. 1A shows a schematic diagram of a traditional fuel converting mechanism of a car.
Figure 1B:
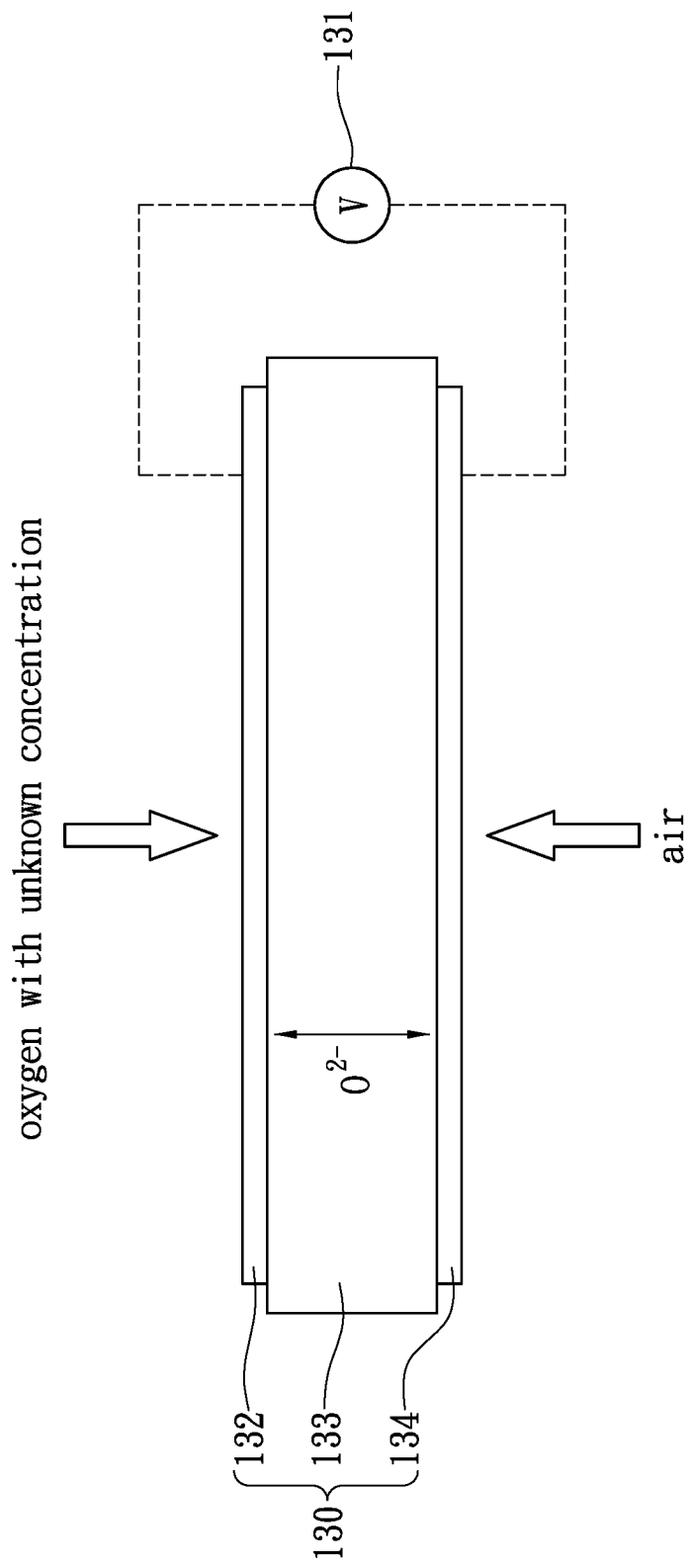
FIG. 1B shows a schematic diagram of a traditional oxygen sensing device.

The conductive catalyst layer 211 of the oxygen sensing unit 21 receives the exhausted gas from the turbine, the exhausted gas may comprise carbon dioxide ($CO_2$), water ($H_2O$), oxides of nitrogen ($NO_x$), hydrocarbons (HC), carbon monoxide (CO), and oxygen ($O_2$). The manner for sensing oxygen of the oxygen sensing device 2 is the same as to the manner for sensing oxygen of the traditional oxygen sensing device 1 (shown in FIG. 1B). It is worth mentioning that the conductive catalyst layer 213 receive the air of atmosphere, the conductive catalyst layer 213 do not receive the gas stored in the gas storing unit 22. The method of the conductive catalyst layer 211 receiving the exhausted gas generated by the internal combustion engine comprises, the gas storing unit 22 receiving the exhausted gas from the turbine, and the judgment circuit 26 controlling the gas storing unit 22 to transmit the exhausted gas to the conductive catalyst layer 211.

Figure 5B:
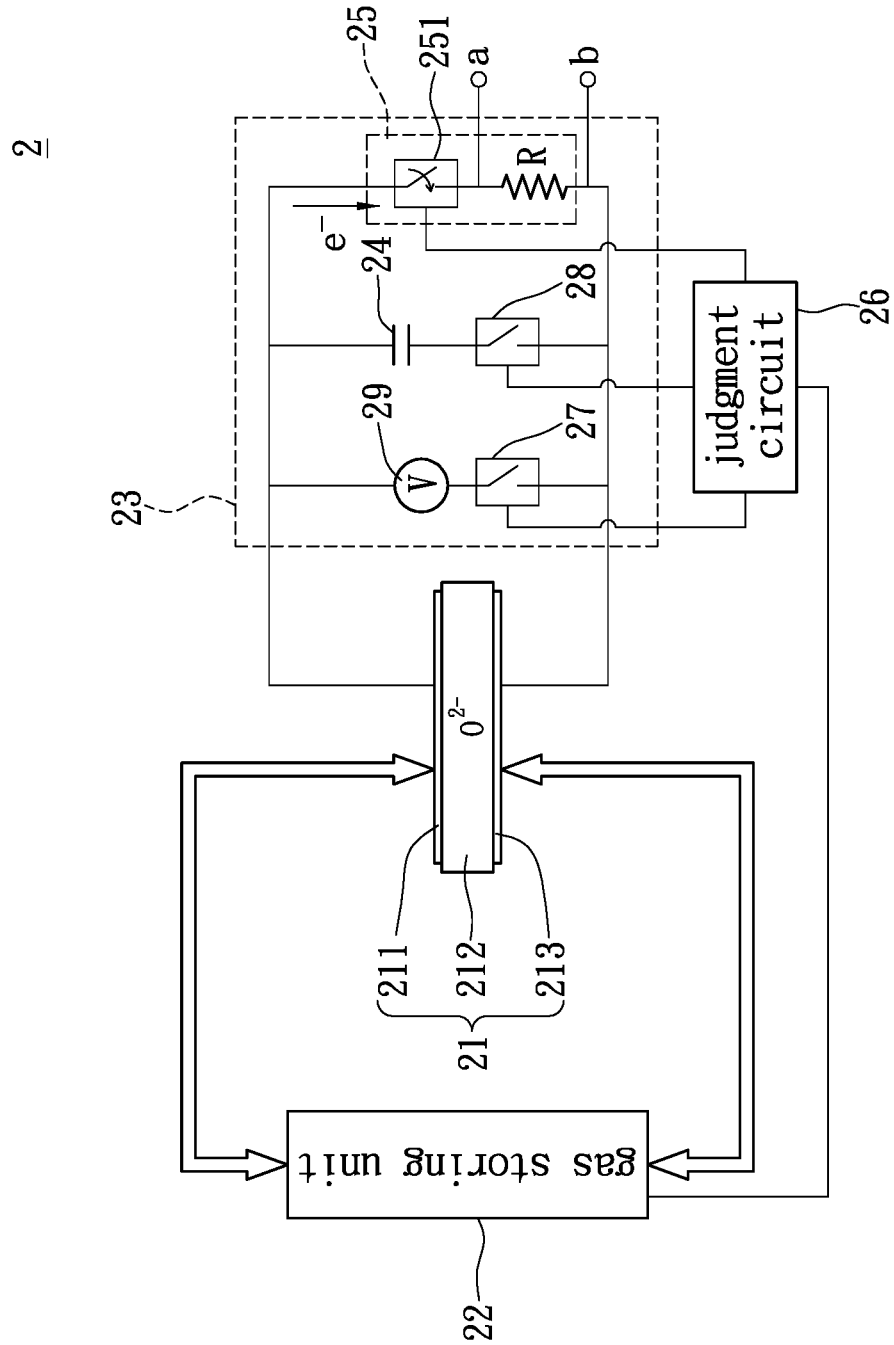
FIG. 5B shows a schematic diagram of a output circuit of an oxygen sensing device outputting electricity according to an embodiment of the instant disclosure.

Please refer to FIG. 5A and FIG. 5B, FIG. 5A shows a schematic diagram of an oxygen sensing unit processing the reaction of hydrocarbons and oxygen according to an embodiment of the instant disclosure, FIG. 5B shows a schematic diagram of a output circuit of an oxygen sensing device outputting electricity according to an embodiment of the instant disclosure. When the oxygen sensing device 2 is used for outputting electricity, hydrocarbons stored in the gas storing unit 22 can make electrochemical catalytic reaction by utilizing the oxygen sensing unit 21 for generating electric current. The electric current may be transmitted to exterior electrical equipment through the power output unit 25. The conductive catalyst layer 211 of the oxygen sensing unit 21 receives hydrocarbons (HC) stored in the gas storing unit 22 and processes the reaction (3): $HC+O^{2-}\rightarrow CO_2+H_2O+2e^-$.

The reaction of hydrocarbons (HC) and oxygen ions ($O^{2-}$) produces carbon dioxide ($CO_2$), water ($H_2O$) and electrons (e−). The oxygen ions ($O^{2-}$) in the solid oxide electrolyte 212 may be replenished through conductive catalyst layer 213 decomposing oxygen of the air into oxygen ions ($O^{2-}$), and the oxygen ions ($O^{2-}$) may be transmitted from the solid oxide electrolyte 212 to the conductive catalyst layer 211. When the judgment circuit 26 controls the switch 251 to accomplish a conducting loop, the electrons (e−) generated in the reaction (3) may outcome electric current for power receiving of the electrical equipment connected to the output terminals a, b of the power output circuit 25. Briefly, the oxygen sensing unit 21 makes the reaction of hydrocarbons (HC) stored in the gas storing unit 22 and oxygen ions for generating electricity to the power output circuit 25.

Figure 6:
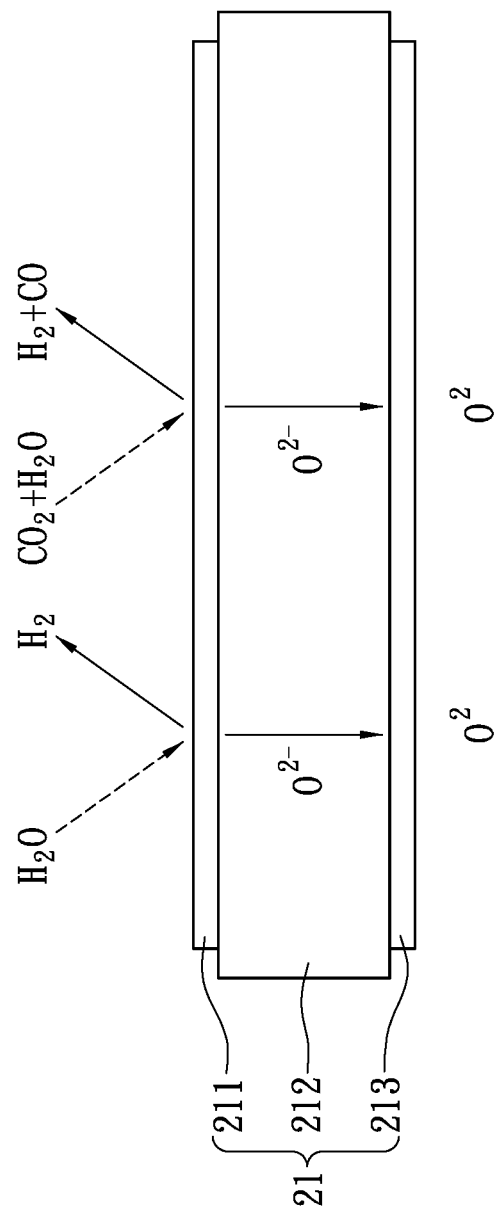
FIG. 6 shows a schematic diagram of an oxygen sensing unit generating hydrogen and monoxide according to an embodiment of the instant disclosure.
Figure 7A:
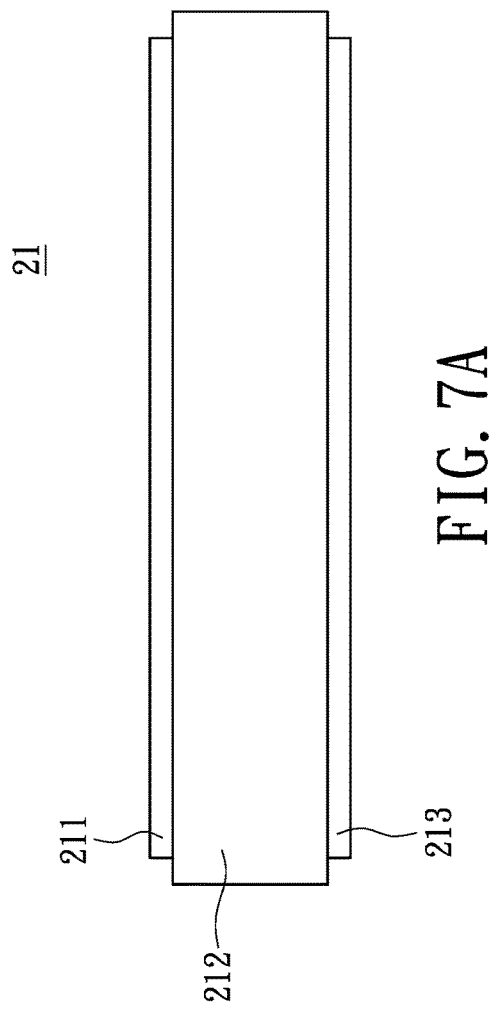
FIG. 7A to FIG. 7D shows a cross-sectional diagram of an oxygen sensing unit according to an embodiment of the instant disclosure.
Figure 7B:
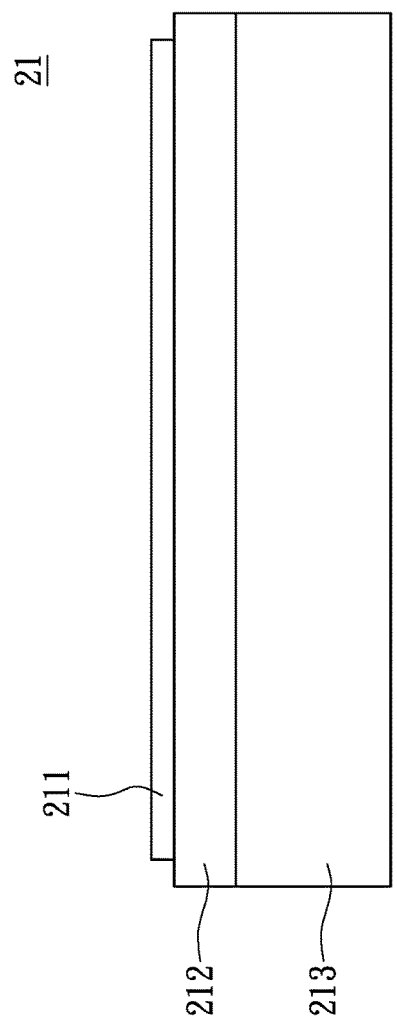
Figure 7C:
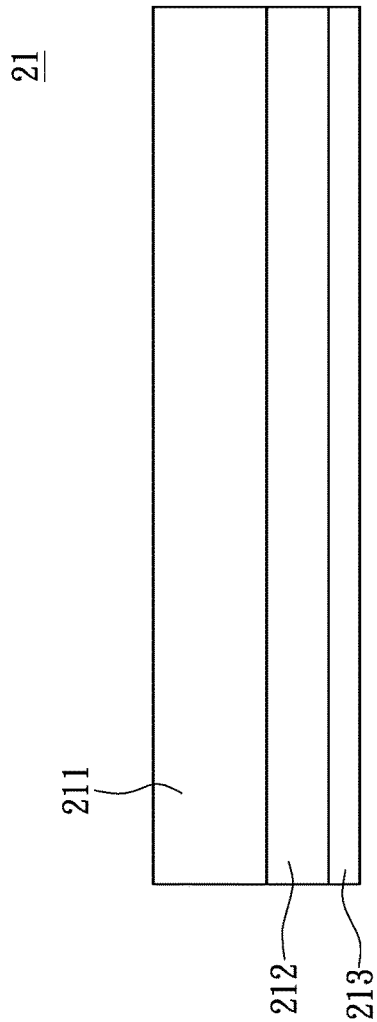
Figure 7D:
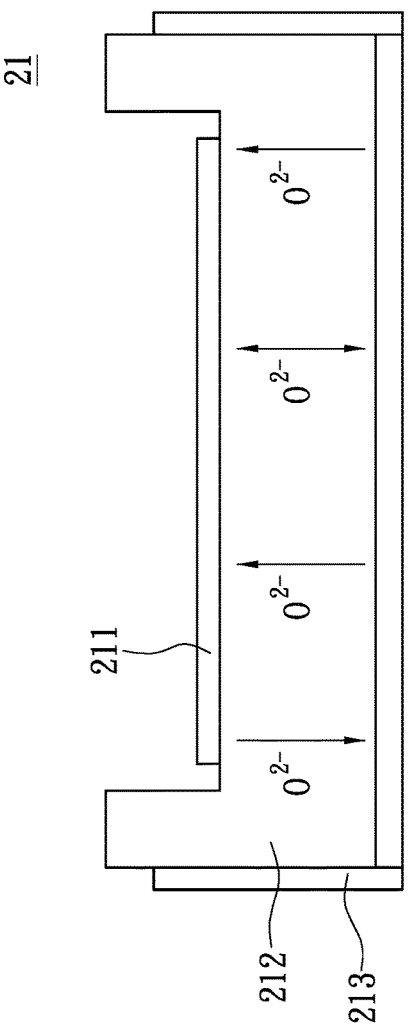

Please refer to FIG. 2 and FIG. 6, FIG. 6 shows a schematic diagram of an oxygen sensing unit generating hydrogen and carbon monoxide according to an embodiment of the instant disclosure. When the electrical power of the power source 24 is excess, the electrical power may be stored in the form of hydrogen ($H_2$) generated by the oxygen sensing unit 21. On the other hand, carbon monoxide (CO) and hydrogen ($H_2$) may be generated from carbon dioxide ($CO_2$) and water ($H_2O$) of the exhausted gas from the internal combustion engine by utilizing the oxygen sensing device 2. The carbon monoxide (CO) and hydrogen ($H_2$) may be upstream material with industrial value, for example, carbon monoxide (CO) and hydrogen ($H_2$) may used to produce chemicals, such as methanol or methane. The judgment circuit 26 of the control unit 23 conducts the switch 28, makes the switch 27, 251 be non-conductive, and makes the exhausted gas stored in the gas storing unit 22 be transmitted to the conductive catalyst layer 211 of the oxygen sensing unit 21. Because power source 24 supplies electrical power , the conductive catalyst layer 211 makes a reaction (4) of the water ($H_2O$) in the exhausted gas and the electrons (e−) from the power source 24 to produce hydrogen ($H_2$), the reaction (4) is described in the following: $H_2O+2e^-\rightarrow H_2+O^{2-}$.

Then, the solid oxide electrolyte 212 transmits the oxygen ions ($O^{2-}$) to conductive catalyst layer 213. The conductive catalyst layer 213 converts the oxygen ions ($O^{2-}$) into oxygen ($O_2$) and transmits excess electrons (e−) to the power source 24. The reaction (4) converts the electricity of the power source 24 into the form of hydrogen ($H_2$) which is green energy replacing fossil fuels. On the other hand, when making carbon monoxide (CO) and hydrogen ($H_2$), the conductive catalyst layer 211 makes a reaction (5) of carbon dioxide ($CO_2$) and water ($H_2O$), the reaction (5) is described in the following: $CO_2+H_2O+4e^-\rightarrow CO+H_2+2O^{2-}$. Briefly, the oxygen sensing unit 21 may use the electricity of the power source 24 to generate hydrogen ($H_2$) for storing energy or generate carbon monoxide (CO).

FIG. 7A to FIG. 7D shows a cross-sectional diagram of an oxygen sensing unit according to an embodiment of the instant disclosure. The oxygen sensing unit 21 may be flat-shaped, such as the shape shown in FIG. 7A to FIG. 7C. A thicker one of the solid oxide electrolyte 212, the conductive catalyst layer 213 or the conductive catalyst layer 211 may utilized to structurally support the oxygen sensing unit 21. The conductive catalyst layer 213 may surrounds the solid oxide electrolyte 212 and the conductive catalyst layer 211 for covering the solid oxide electrolyte 212 and the conductive catalyst layer 211. The shape of the conductive catalyst layer 213 may be a cone, a tube, or the shape shown in FIG. 7D, as long as the solid oxide electrolyte 212 is between the conductive catalyst layer 211 and the conductive catalyst layer 213. Briefly, the shapes of the conductive catalyst layer 211 and the conductive catalyst layer 213 are not restricted, as long as the solid oxide electrolyte 212 is between the conductive catalyst layer 211 and the conductive catalyst layer 213. The solid oxide electrolyte 212 may transmits oxygen ions ($O^{2-}$) between the conductive catalyst layer 211 and the conductive catalyst layer 213. On the other hand, the solid oxide electrolyte 212 may not contact tightly the conductive catalyst layer 211 and the conductive catalyst layer 213, and an air gap could be existed between the solid oxide electrolyte 212 and the conductive catalyst layer 211 (or conductive catalyst layer 213). The air gap may filled with air, thus the aforementioned reactions still could be processed.

Figure 8:
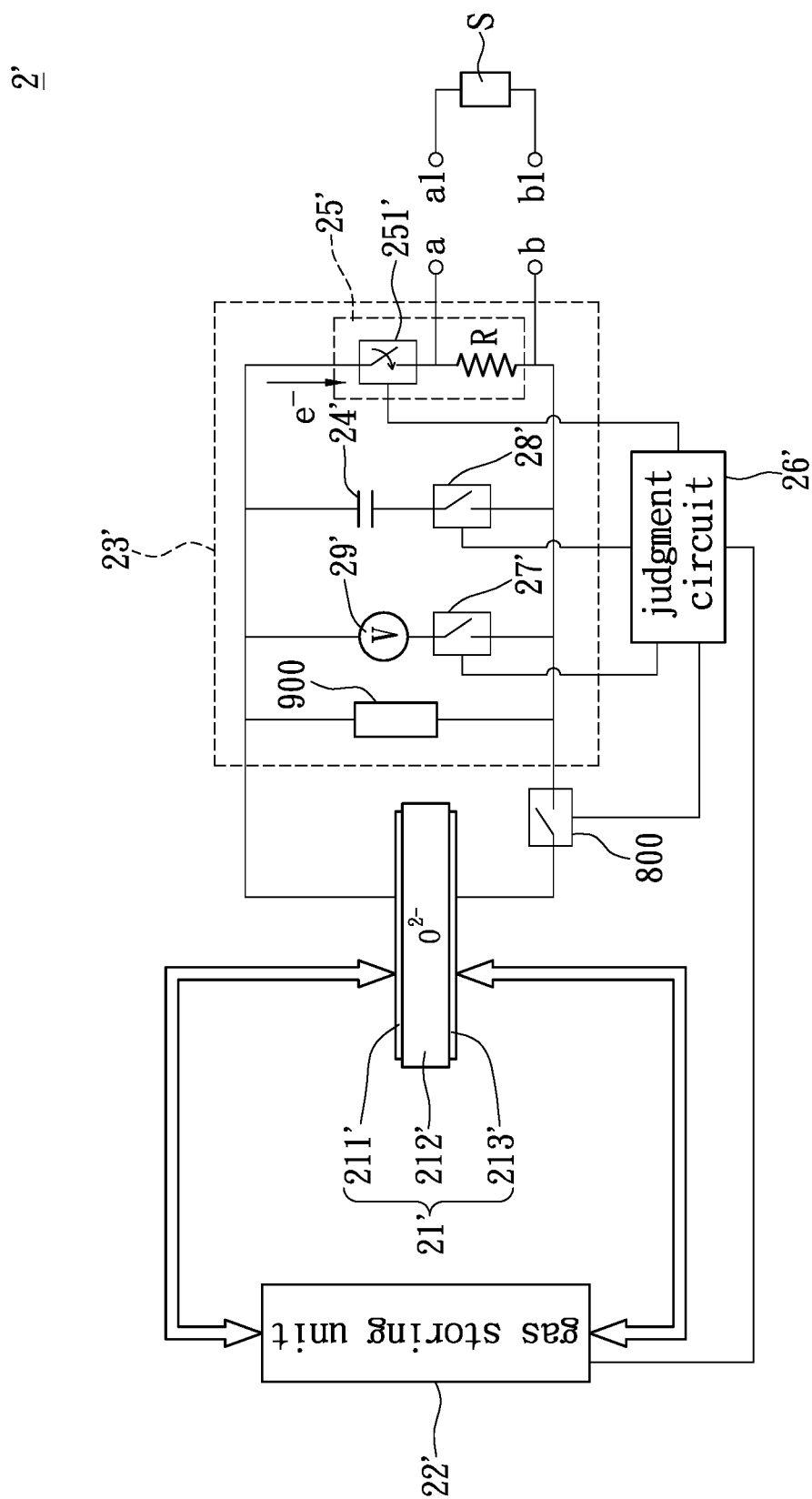
FIG. 8 shows a schematic diagram of an electrochemical catalytic converter for a vehicle according to an embodiment of the instant disclosure.

Referring to FIG. 8, FIG. 8 shows a schematic diagram of an electrochemical catalytic converter for a vehicle according to an embodiment of the instant disclosure.

The electrochemical catalytic converter for a vehicle 2' is mounted on an exhaust pipe of a vehicle for converting the emission. The electrochemical catalytic converter for a vehicle 2' includes an converting unit 21', a gas storing unit 22', a control unit 23', and a control switch 800. The converting unit 21' includes a solid oxide electrolyte 212', a conductive catalyst layer 211' and a conductive catalyst layer 213'. In the embodiment, the manner for the converting unit 21' is the same as the manner for the oxygen sensing unit 21 of the above embodiment.

The control unit 23' includes a power source 24', a voltmeter 29', a power output circuit 25', a judgment circuit 26', a first switch 27', a second switch 28' and a voltage regulator 900. The power output circuit 25' includes a switch 251' and a resistor R. In the embodiment, the power source 24' is a rechargeable battery. In the embodiment, the power source 24' is used for initializing the converting unit 21' to process the exhausted gas of the vehicle.

In the embodiment, one end of the voltage regulator 900, one end of the voltmeter 29', one end of the power source 24' are electrically connected to the conductive catalyst layer 211' of the converting unit 21'. The other end of the voltage regulator 900 is electrically connected to the conductive catalyst layer 213' through the control switch 800. The other end of the voltmeter 29' is electrically connected to the first switch 27'. In other words, the voltmeter 29' is electrically connected to the conductive catalyst layer 213' through the first switch 27' and the control switch 800. The other end of the power source 24' is electrically connected to the second switch 28'. The power source 24' is electrically connected to the conductive catalyst layer 213' through the second switch 28' and the control switch 800. One end of the resistor R is electrically connected to the conductive catalyst layer 211' through the switch 251', and other end of the resistor R is electrically connected to the conductive catalyst layer 213' through the control switch 800.

The judgment circuit 26' controls the control switch 800, the first switch 27', the second switch 28', and the switch 251' according to different states.

In the first state, the converting unit 21' receives the exhausted gas of the vehicle, such as oxides of nitrogen ($NO_x$) and carbon monoxide (CO), and processes a catalytic reaction to generate gas of the above embodiment. When the control switch 800 is turned on (ON state) and the switch 251' is turned on, the electric power generated by the converting unit 21' is provided to charge the power source 24' (rechargeable battery). When the power source 24' is fully charged, the judgment circuit 26' turns off the second switch 28'.

In the embodiment, the electrochemical catalytic converter for a vehicle further includes a backup battery S. The backup battery S is electrically connected to the resistor R through the two ends a1, b1 thereof. Therefore, the converting unit 21' can provide the electric power to the backup battery S connected to the resistor R. The backup battery S is used for storing the electric power generated by the converting unit 21' as a jump-starter.

In the second state, the control switch 800 is turned on, the switch 251' is turned off, and the backup battery S is disconnected from the terminal a and the terminal b of the power output circuit 25'. The power source 24' provides the electric power to the converting unti 21' to process the reaction (1), the reaction (2) or the reaction (4) of the above embodiment. Those gases of the above reactions are stored in the gas storing unit 22'.

In the third state, when the starting battery of the vehicle is discharged, the backup battery S is used for boosting the vehicle. In the second state, the control switch 800 is turned off, and the backup battery S provides an electric power with a large current to boost the vehicle.

In the other embodiment, the resistor R can be directly connected to the starting battery of the vehicle. In general, the electrochemical catalytic converter for a vehicle 2' can generate the electric power to charge the starting battery of the vehicle. In urgent case, the electrochemical catalytic converter for a vehicle 2' can use the gas stored in the gas storage unit 22' to generate the electric power for boosting the vehicle. The voltage regulator 900 can be used for boosting the voltage of the electric power generated by the converting unit 21'. In the embodiment, the voltmeter 29' can detect whether the backup battery S is fully charged. When the backup battery S is fully charged, the switch 251' is turned off by the judgement circuit 26'.

In the embodiment, the judgement circuit 26' detects the volume of the gas stored in the gas storage unit 22' and calculates the electric power converted by the gas stored in the gas storage unit 22'.

When the gas stored in the gas storage unit 22' is less than a threshold value, the judgment circuit 26' transmits a notice signals to the in-vehicle computer (not shown in figures) to notice the user. The control switch 800 is turned off by the judgement circuit 26' for reducing the leakage current. In the embodiment, the gas storage unit 22' is replaceable. When the gas stored in the gas storage unit 22' is greater than an upper threshold value, the user can use an empty gas storage unit 22' to replace the full gas storage unit 22'.

In addition, when the engine of the vehicle is not running, there is no exhausted gas transmitting to the converting unit 21', The control switch 800 is also turned off (OFF state) by the judgement circuit 26'. In summary, according to the aforementioned embodiments, the oxygen sensing device may process electrochemical catalytic reactions, oxygen sensing, electrical power generation, electrolysis for storing energy and electrolysis for making carbon monoxide (CO). Therefore, the exhausted gas could be reduced and be used to generate electricity, or syngas (including hydrogen and carbon monoxide) could be made. The user may make the oxygen sensing unit to process required chemical reaction through controlling judgment circuit. The electrochemical catalytic converter for a vehicle in the present disclosure can not only reduce the air pollution generated by the exhausted gas of the vehicle, but also can be used as a power charger or a jump-starter to boost the vehicle when the starting battery of the vehicle is discharged.

The descriptions illustrated supra set forth simply the preferred embodiments of the instant disclosure; however, the characteristics of the instant disclosure are by no means restricted thereto. All changes, alternations, or modifications conveniently considered by those skilled in the art are deemed to be encompassed within the scope of the instant disclosure delineated by the following claims.

What is claimed is:

1. An electrochemical catalytic converter for a vehicle, comprising:
   a converting unit, comprising:
      a first conductive catalyst layer;
      a second conductive catalyst layer; and
      a solid oxide electrolyte, disposed between the first conductive catalyst layer and the second conductive catalyst layer;
   a control switch, electrically connected to the second conductive catalyst layer;
   a gas storing unit, for storing a first specific gas generated by the converting unit; and
   a control unit, electrically coupled to an oxygen sensing unit, comprising:
      a voltmeter, for detecting a voltage of the converting unit, wherein the voltmeter is electrically connected to the first conductive catalyst layer and the second conductive catalyst layer through a first switch and the control switch;
      a power output circuit, for outputting an electric power, wherein the converting unit causes a reaction of the hydrocarbons stored in the gas storing unit for generating the electric power to the power output circuit, wherein the power output circuit further comprises:
         a third switch;
         a resistor, electrically connected to the third switch, wherein the two ends of the resistor are connected to a backup battery;
         a voltage regulator, one end of the voltage regulator being electrically connected to the converting unit, and the other end of the voltage regulator being electrically connected to the control switch;
      a power source, wherein the power source is electrically connected to the first conductive catalyst layer and the second conductive catalyst layer through a second switch and the control switch; and
      a judgment circuit, for adjusting the conducting status of the control switch, the first switch, the second switch and the third switch according to different states of the electrochemical catalytic converter for a vehicle;
   when the control switch is turned off, the backup battery provides an electric power to boost the vehicle when a starting battery of the vehicle is discharged, and
   when the control switch is turned on, the voltage regulator is used for boosting the voltage of the electric power generated by the converting unit to charge the starting battery.

2. The electrochemical catalytic converter for a vehicle of claim 1, further comprising the backup battery, electrically connected to the power output circuit, wherein the control switch is turned on, and the converting unit receives exhausted gases of the vehicle to generate an electric power to charge the backup battery.

3. The electrochemical catalytic converter for a vehicle of claim 1, wherein the control switch is turned on, the power source provides an electric power to the converting unit to generate the specific gas and stores the specific gas in the gas storing unit.

4. The electrochemical catalytic converter for a vehicle of claim 1, wherein the power output circuit is electrically connected to the starting battery of a vehicle and the control switch is turned on, the electrochemical catalytic converter for a vehicle provides an electric power to boost the vehicle when the starting battery of the vehicle is discharged.

5. The electrochemical catalytic converter for a vehicle of claim 1, wherein the power source is charged by the converting unit when the converting unit receives exhausted gases of the vehicle to generate the specific gas, the control switch is turned on and the second switch is turned on, when the power source is fully charged, the second switch is turned off.

6. The electrochemical catalytic converter for a vehicle of claim 1, wherein the judgment circuit configures whether the converting unit utilizes the electric power of the power source to generate carbon monoxide and hydrogen.

7. The electrochemical catalytic converter for a vehicle of claim 1, wherein when the judgment circuit determines to make the electric power of the power source be applied for generating carbon monoxide, the judgment circuit controls the power source to provide the electric power to the converting unit, the converting unit utilizes the electric power to make the carbon dioxide stored in the gas storing unit react with the water molecules to generate monoxide and hydrogen.

* * * * *